US011923077B2

(12) United States Patent
Abadir

(10) Patent No.: US 11,923,077 B2
(45) Date of Patent: *Mar. 5, 2024

(54) RESOURCE EFFICIENT COMPUTER-IMPLEMENTED SURGICAL RESOURCE ALLOCATION SYSTEM AND METHOD

(71) Applicant: Aspire Smart Health-Lancaster, LLC, Lancaster, PA (US)

(72) Inventor: Essam Abadir, Lancaster, PA (US)

(73) Assignee: Aspire Smart Health-Lancaster, LLC, Lancaster, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,516

(22) Filed: Jul. 1, 2022

(65) Prior Publication Data

US 2022/0336089 A1 Oct. 20, 2022

Related U.S. Application Data

(60) Continuation of application No. 16/691,088, filed on Nov. 21, 2019, now Pat. No. 11,393,581, which is a
(Continued)

(51) Int. Cl.
*G16H 40/20* (2018.01)
*G06Q 10/0631* (2023.01)
(Continued)

(52) U.S. Cl.
CPC ..... *G16H 40/20* (2018.01); *G06Q 10/063112* (2013.01); *G06Q 10/063116* (2013.01);
(Continued)

(58) Field of Classification Search
CPC .......... G06Q 50/22–24; G16H 40/20
See application file for complete search history.

(56) References Cited

U.S. PATENT DOCUMENTS

| 5,549,117 A | 8/1996 | Tacklind et al. |
| 6,389,454 B1 * | 5/2002 | Ralston ............... G06Q 10/109 709/204 |

(Continued)

FOREIGN PATENT DOCUMENTS

| JP | 2017021641 A | 1/2017 |
| KR | 2016-0144570 A | 12/2016 |
| WO | 2014210603 A2 | 12/2014 |

OTHER PUBLICATIONS

42 CFR 101.952 (f) (Year: 2012).*
(Continued)

*Primary Examiner* — John A Pauls
(74) *Attorney, Agent, or Firm* — Fox Rothschild LLP

(57) ABSTRACT

Embodiments generally relate to a surgical resource allocation system. Patients seeking a procedure can use the system to identify surgeons and surgical facilities. The patient can then use the system to book the procedure with a selected surgeon at a selected facility. In an example, a patient can indicate a need for a certain procedure. The patient can then provide criteria for a surgeon or facility, such as a desired location, desired time, surgeon rankings, and facility rankings. The system can then identify surgeons and facilities that match the criteria and present them for selection by the patient. The patient can then select the surgeon and facility with which the patient would like the procedure performed. With the surgeon and facility selected, the patient can then choose to book the procedure.

11 Claims, 8 Drawing Sheets

Related U.S. Application Data division of application No. 15/471,346, filed on Mar. 28, 2017, now Pat. No. 11,670,413.

(51) Int. Cl.

| | |
|---|---|
| G06Q 10/0639 | (2023.01) |
| G16H 10/20 | (2018.01) |
| G16H 20/40 | (2018.01) |
| G16H 50/30 | (2018.01) |

(52) U.S. Cl.
CPC ....... *G06Q 10/06398* (2013.01); *G16H 10/20* (2018.01); *G16H 20/40* (2018.01); *G16H 50/30* (2018.01)

(56) References Cited

U.S. PATENT DOCUMENTS

| | | | |
|---|---|---|---|
| 2002/0133375 A1 | 9/2002 | Moore et al. | |
| 2004/0039626 A1* | 2/2004 | Voorhees | G06Q 10/1095 |
| | | | 705/7.19 |
| 2004/0249674 A1* | 12/2004 | Eisenberg | G16H 40/20 |
| | | | 705/2 |
| 2005/0060201 A1* | 3/2005 | Connely | G06Q 10/10 |
| | | | 705/2 |
| 2006/0143060 A1* | 6/2006 | Conry | G16H 40/20 |
| | | | 705/7.19 |
| 2007/0011032 A1 | 1/2007 | Bregante et al. | |
| 2008/0015896 A1* | 1/2008 | Reynolds | G06Q 10/10 |
| | | | 705/2 |
| 2008/0027754 A1* | 1/2008 | Auker | G16H 40/63 |
| | | | 705/2 |
| 2008/0065726 A1* | 3/2008 | Schoenberg | G06F 16/9535 |
| | | | 709/205 |
| 2008/0133290 A1 | 6/2008 | Siegrist et al. | |
| 2008/0147436 A1 | 6/2008 | Ohlsson | |
| 2009/0094064 A1 | 4/2009 | Tyler et al. | |
| 2009/0198733 A1 | 8/2009 | Gounares et al. | |
| 2012/0303695 A1* | 11/2012 | Michel | H04W 4/50 |
| | | | 709/203 |
| 2013/0339969 A1* | 12/2013 | Koski | G06Q 10/10 |
| | | | 718/103 |
| 2014/0288941 A1 | 9/2014 | Roady | |
| 2015/0178648 A1 | 6/2015 | Iqbal et al. | |
| 2015/0248528 A1 | 9/2015 | O'Fallon et al. | |

OTHER PUBLICATIONS

The effect of matching comprehensive services to patients' needs on drug use improvement in addiction treatment; Friedman et al.; Jun. 24, 2004 (Year: 2004).*

42 CFR Chapter V Section 1001.952 Oct. 1, 2012 Version (Year: 2012).

Friedman, P.D. et al., "The effect of matching comprehensive services to patients' needs on drug use improvement in addiction treatment", Addiction (Jun. 24, 2004), 99(8):962-972 (abstract).

* cited by examiner

RESOURCE EFFICIENT COMPUTER-IMPLEMENTED SURGICAL RESOURCE ALLOCATION SYSTEM AND METHOD

CROSS-REFERENCE TO RELATED APPLICATION

This application is a continuation of U.S. Patent Application No. 16/691,088 filed Nov. 21, 2019, which is a divisional of U.S. Patent Application No. 15/471,346 filed Mar. 28, 2017, the disclosures of which are hereby incorporated by reference in their entirety.

BACKGROUND

When seeking a surgical procedure, a patient is often tasked with identifying a surgeon to perform the procedure and facilities at which the surgery is to be performed. This can be a resource-intensive process for the patient. From the facilities and surgeon side, the process can be inefficient. There is exists a need in the art for an improvement to matching patients, surgeons, and surgical facilities that overcome the challenges of prior systems, including challenges relating to the consumption of computing resources.

SUMMARY

In general terms, this disclosure is relevant to a resource efficient computer-implemented surgical resource allocation system and method. In one possible configuration and by non-limiting example, a method includes acquiring surgical facility data regarding two or more surgical facilities; receiving a request for surgical services for a patient from a client device, the request including patient parameters; and generating one or more matches between surgeons and surgical facilities based in part on the surgical facility data and the patient parameters.

Various aspects are described in this disclosure, which include, but are not limited to, the following aspects.

In one aspect, a method for generating matches between surgeons and surgical facilities includes: acquiring surgical facility data for two or more surgical facilities, wherein acquiring the surgical facility data comprises establishing a connection with an application programming interface of a medical scheduling service associated with at least one of the surgical facilities; acquiring surgeon data for two or more surgeons, wherein the surgeon data comprises schedule data for at least one of the surgeons; receiving, from a client device, a request for surgical services for a patient, the request comprising patient parameters; and generating one or more matches between a surgeon and a surgical facility based in part on the surgical facility data, the surgeon data, and the patient parameters.

In yet another aspect there is a method for using sanitized data for generating a reward model for surgeons. The method includes: for each respective surgeon of a set of surgeons: acquiring reward model data, the reward model data comprising population health data associated with patients treated by the respective surgeon; sanitizing the reward model data, wherein sanitizing the reward model data comprises ensuring that flagged data is isolated from the reward model data; and generating a reward model using the sanitized reward model data.

DETAILED DESCRIPTION

Figure 1:
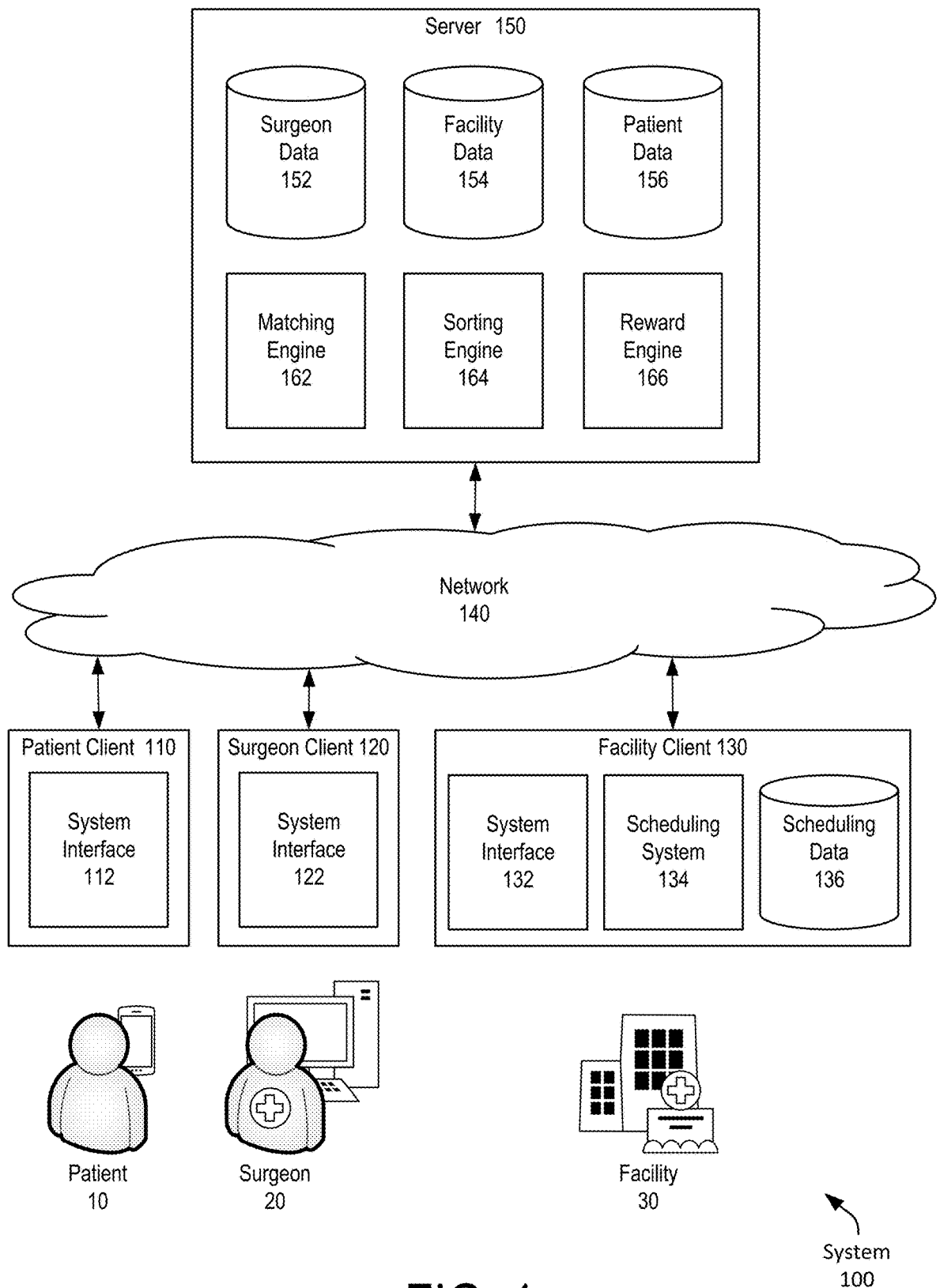
FIG. 1 illustrates an example surgical resource allocation system.

Disclosed embodiments generally relate to a surgical resource allocation system. Patients seeking a medical procedure can use the system to identify surgeons and surgical facilities. The patient can then use the system to book the procedure with a selected surgeon at a selected facility.

In an example, a patient can indicate a need for a certain procedure. The patient can then provide his or her criteria for a surgeon or facility, such as a desired location, desired time, surgeon rankings, and facility rankings. The systems can then identify surgeons that match the criteria and provide the identified surgeons to the patient for selection. The patient can select one or more surgeons. The system can then identify facilities at which the patient-selected surgeons can perform the procedure. These identified facilities are presented to the patient for selection. The patient then selects one or more facilities from the identified facilities. The system can then use the patient-selected facilities and surgeons to generate matches between surgeons and facilities and present the matches to the patient for final selection. The patient can then select the surgeon-facility match with which the patient would like the procedure performed.

With the surgeon and facility selected, the patient can then choose to book the procedure. The system can be integrated with the scheduling, booking, or billing procedures of surgeons and facilities to facilitate the process.

In another example, the system can provide the patient with facilities to select from first, and then provide the patient with surgeons to select from second. In yet another example, the system provides the patient with matches between surgeons and facilities, rather than letting the patient choose them one at a time.

When presenting facilities, surgeons, or matches therebetween to the patient, the system can sort the presented items based on a variety of attributes, including but not limited to: price, dates, distance, surgeon attributes, facility attributes, reviews (e.g., based on patient satisfaction surveys), and other attributes.

As an incentive for surgeons to participate in the system and improve their quality ratings, participating surgeons can have the opportunity to earn rewards. The rewards can be based on a reward model that takes into account various data. In an example, this data includes surgeon quality scores and a number of patient satisfaction surveys completed by patients of the respective surgeons. In another example, the reward model can take into account data received from passive data collection methods, such as biometric data gathered from devices with biometric sensors, such as wearable devices. The biometric data can be used to infer patient anxiety or other patient health information. In some examples, the passive data collection can inform surgeon or facility attributes, which can be used as part of the reward and other processes. The rewards can be funded by, for example, subscription fees and advertising revenue.

Disclosed embodiments can be relevant to overcoming technical problems with existing techniques for matching patients with surgeons and facilities.

For example, when searching for a surgeon and facility for a surgical procedure, traditionally a prospective patient would need to search for and contact (often electronically) each surgeon and surgical facility individually. This would result in an increase in computing resource consumption and higher network use. This can result in inefficiencies when performing searches because it requires increased network resource consumption to research and contact potential surgeons and facilities (e.g., increased use of the network for online searches, and Internet-based messaging, such as email). In addition, for security, privacy, or other reasons, the patient may not have access to the scheduling and other resources necessary to assist in the process of matching surgeons and facilities.

Alternatively, the patient could delegate to someone else but the patient would lose flexibility and control over the process. Further, the service to which the task is delegated would also consume additional computing resources.

In contrast to traditional systems, the disclosed centralized surgical resource allocation system can be a centralized resource that is independent from particular surgeons and facilities. In this manner, the system can provide the patient increased customization options at a decreased computing resource cost. For example, by working directly with a centralized information repository and matching service, the patient consumes fewer networking resources because the patient interacts with a single, centralized resource. In addition, by interacting with a single, centralized resource, there is a reduced risk of unintentional or erroneous inputs from the patient. For example, if the patient contacts ten different facilities and ten different surgeons regarding a procedure, there is an increased risk that the user makes a typo or other mistake compared to entering the information once at a central server.

The centralized nature of the server can also provide security advantages. For example, rather than allowing patients to access the schedules and other information of surgeons and facilities, this information can be securely stored at the central server. The server can then provide access to this information in a usable form to the patient without unnecessarily exposing other sensitive data to the patient. In another example, rather than the patient sending medical information to multiple different prospective surgeons and facilities, the patient sends the medical information to a single, centralized service. In this manner, the patient does not need to spread copies of the data to multiple locations, which can cause data security issues.

There are also regulatory challenges associated with matching surgeons and facilities. For example there are federal regulations surrounding physician referrals. See, e.g., 42 U.S.C. § 1395nn. The embodiments discussed herein can overcome some or all of these regulatory challenges.

In an example the referral and reward service can be a separate party from the surgeons and the facilities. Further, a reward system can compensate surgeons based on a fair market value for services provided and not based on a value or volume of referrals or other business generated for the facility at which the surgeon provided services. Advantageously this can help alleviate regulatory challenges regarding the physician referral. Further the reward system and any associated compensation agreement can be provided in writing and signed by all parties. The reward agreement can specify the services covered by the agreement.

Aspects of disclosed embodiments can also provide both technical and regulatory advantages. For example, when performing matching, when determining compensation for physicians, and during other processes there can be regulatory prohibitions on particular kinds of data being used. For example, it may be prohibited to use the value or volume of referral data to determine compensation. Disclosed embodiments can isolate prohibited data from non-prohibited data or otherwise sanitize data used in the reward calculations. By performing the calculations in a smaller subset of data, the reward calculation using the sanitized data would require fewer processing cycles to complete and less memory to store because less data is being factored in to the reward calculation process.

While reference is made to "patients," the patient need not be a patient associated with any particular doctor, surgeon, or facility. The patient can be a prospective patient. Further, the person using the system need not be the patient on which the procedure will be performed. For example, someone else can participate in the systems and methods described herein on behalf of the patient.

Throughout this specification reference is made to "surgeons." In an example, the surgeon may be a person capable of performing a surgical procedure or a person accessing the system on behalf of the surgeon (e.g., a member of the surgeon's administrative staff). In another example, the surgeon need not be a surgeon and may instead be another kind of healthcare professional, such as a doctor, nurse, or dentist.

As used herein "facilities" can refer to one or more resources associated with a healthcare facility. The resources can include rooms associated with procedures (e.g., operating rooms, recovery wards, consulting spaces, etc.), staff (e.g., nurses, maintenance personnel, etc.), supplies (e.g., surgical instruments, medication, bedding, etc.), and administrative resources, among others.

Disclosed embodiments are primarily discussed in relation to surgical procedures performed on patients at healthcare facilities. However, the techniques described herein need not be so limited. Disclosed techniques and embodiments may be modified to apply outside of the healthcare space. As another example, rather than being a patient seeking medical services, the user can be a person seeking fitness, tutoring, legal, or accounting services from a personal trainer, tutor, accountant, lawyer, or other person at a particular location.

FIG. 1 illustrates an example surgical resource allocation system 100. The surgical resource allocation system 100 can allocate resources among one or more patients 10, surgeons 20, and facilities 30. For example, the system 100 can match one or more patients 10 seeking a surgical procedure with one or more surgeons 20 to perform the procedure and one or more facilities 30 at which the procedure can take place.

The system 100 can include a patient client 110, a surgeon client 120, and a facility client 130. The patient client 110, the surgeon client 120, and the facility client 130 can be connected over a network 140, such as the Internet, to a server 150. The server 150 can be used to perform resource allocation tasks for the system 100. For example, the server 150 can match patients 10 with surgeons 20 and facilities 30.

The patient client 110 can be a computing device that the patient 10 can use to interact with one or more other components of the system 100. Examples of a patient client 110 can include a smartphone, a tablet, a desktop computer, or a laptop computer. In some examples, the patient client 110 can be a personal computing device of the patient 10. In other examples, the patient client 110 can be a computing environment provided to patient 10, such as a kiosk at a medical facility provided for booking procedures.

The patient client 110 can provide a system interface 112 over which the patient 10 can interact with other parts of the system 100 to, for example, find and book a surgeon and facility match for surgical procedure. The system interface 112 can include, for example, an interface of a website, an interface of software running on the patient client 110, an interface of a remotely-hosted application (e.g., a web application) accessed using the patient client 110.

In an example, the patient 10 can use a smart phone to launch an application that connects to the server 150 for booking a surgical procedure. The patient 10 can then use the smart phone application to locate surgeons 20 and facilities 30, find a match, and book the match. In this example, the smart phone of the patient 10 is being used as the patient client 110, and the smart phone application functions as the system interface 112.

The surgeon client 120 can be a computing device. A surgeon 20 can use the surgeon client 120 to interact with one or more other parts of the system 100. Examples of the surgeon client 120 can include, but need not be limited to, a smartphone, a tablet, a desktop computer, or a laptop computer. The surgeon client 120 can provide a system interface 122 over which the surgeon 20 can interact with other parts of the system 100. The system interface 122 can include, for example, a user interface of a website, a user interface of software running on the surgeon client 120, a user interface of a remotely-hosted application (e.g., a web application) accessed using the surgeon client 120.

An example, the surgeon 20 can use a desktop computer to run software that accesses the server 150 to facilitate booking surgical procedures. For example, the software can allow the surgeon 20 to manage his or her schedule, view booking requests, or update a surgeon profile, among other activities. In a particular example, the software can be an email client where the surgeon 20 can receive emails associated with the server 150. In these examples, the desktop computer of the surgeon 20 is the surgeon client 120, and the software is the system interface 122.

The facility client 130 can be one or more computing devices. One or more administrators, employees, or other representatives of a facility 30 can use the facility client 130 to interact with one or more other parts of the system 100. The facility client 130 can be, but is not limited to, a smartphone, a tablet, a desktop computer, or a laptop computer. The facility client 130 can provide a system interface 132 over which the representative of the facility 30 can interact with other parts of the system 100. The system interface 132 can include, for example, a user interface of a website, a user interface of software running on the facility client 130, a user interface of a remotely-hosted application (e.g., a web application) accessed using the surgeon client 120, or a voice interface.

The facility client 130 can include a scheduling system 134 that can be used to manage one or more resources of the facility 30. For example, the scheduling system 134 can be used to schedule activities of an operating room (e.g., pre-operative setup, performance of an operation, sanitation, maintenance, etc.), schedule staff (e.g., surgeons, anesthesiologists, nurses, maintenance personnel, sanitation personnel, etc.), and manage inventory (e.g., surgical tools, medication, bedding, etc.). An example of a scheduling system 134 can include OPTIME provided by EPIC SYSTEMS CORP. of Madison, Wis. The scheduling system 134 can interact with scheduling data 136.

While the scheduling system 134 and the scheduling data 136 are illustrated as being part of the facility client 130, they need not or need not entirely be. For example, some or all of the scheduling system 134 and scheduling data 136 may be hosted or stored remotely from the facility client 130. In an example, some or all of the scheduling system 134 and the scheduling data 136 can be hosted by the server 150.

The server 150 can include or otherwise be able to access surgeon data 152, facility data 154, patient data 156, a matching engine 162, a sorting engine 164, and a reward engine 166.

This surgeon data 152 can include data regarding surgeons 20 registered with the system 100. For example, to be able to be selected for matches, surgeons 20 may be required to register with the server 150 and provide information. This can include providing, among other things, authentication information (e.g., a username, password, personal identification number, etc.), contact information (e.g., an address, a telephone number, an email address, etc.), licensing information, bibliographic information, metadata regarding surgeries performed, and other data. The information may also include data regarding to which facilities 30 the surgeon 20 has admitting privileges or is otherwise able or willing to perform procedures. This data can be stored as part of the surgeon data 152.

The surgeon data 152 can also include data regarding surgeons that are not registered with the server 150. For example data can be collected from third-party data sources regarding the surgeons 20, which can then be stored as part of the surgeon data 152. Data from third-party data sources can also be collected for surgeons that are registered with the system.

The facility data 154 can include data regarding facilities 30 that are registered with the server 150. For example, when registering with the system, facilities 30 may be required to provide data regarding the kind of resources provided by the particular facility (e.g., a size of rooms provided, a type of rooms provided, a type of surgical instruments provided, a number of support staff provided, type of support staff provided, etc.), a location of the facility, billing information, or other data. The facilities 30 when registering with the system may also be required to provide scheduling information, such as times when particular resources are available. In an example, the facilities 30 can provide access to their respective scheduling systems 134.

The facility data 154 can also include information regarding facilities 30 that are not registered with the server 150. For example, the facility data 154 can include data gathered from third-party data sources. For example, such data can include reviews, mapping information, compliance information, regulatory information, or other data.

The patient data 156 can include data regarding patients 10 that are registered with the system 100. For example, when registering with the system, patients 10 may be required to provide authentication information (e.g. username, password, a personal identification number, two factor authentication information, etc.), contact information (e.g. an address, phone number, an email address, etc.), billing information, insurance information, or other information. The patient data 156 may also include personal health information of patients 10, such as details regarding the medical history.

The patient data 156 can also include information retrieved from third-party resources. For example, after patient 10 registers with the server 150, the server 150 can retrieve information regarding the patient 10 from third-party data resources. For instance, the server 150 can access health information of the patient 10 stored by third party using credentials provided by the patient 10.

In some examples, patients 10 can provide permission for the server 150 to access patient health information, take actions on behalf of the patient 10 (e.g., book surgical procedures), or to perform other activities that may require permission. Information regarding this permission and any credentials associated therewith may be stored with the patient data 156.

The matching engine 162 can generate matches among one or more patients 10 and one or more surgeons 20. The matching engine 162 can generate matches among one or more patients 10 and one or more facilities 30. The matching engine 162 can generate matches among one or more surgeons 20 and one or more facilities 30. The matching engine 162 can generate matches among one or more patients 10, one or more surgeons 20, and one or more facilities 30.

The matching engine 162 can receive a variety of data as input into the matching process, including but not limited to the surgeon data 152, the facility data 154, and the patient data 156. The matching engine 162 will be discussed in greater detail in conjunction with FIG. 2 and FIG. 3.

The sorting engine 164 can sort one or more matches based on a variety of criteria. The sorting engine 164 will be discussed in greater detail in conjunction with FIG. 2 and FIG. 4.

The reward engine 166 can generate a reward model with which one or more surgeons 20 and one or more facilities 30 can be rewarded. The reward engine 166 will be discussed in greater detail in conjunction with FIG. 2, FIG. 5, and FIG. 6.

Figure 2:
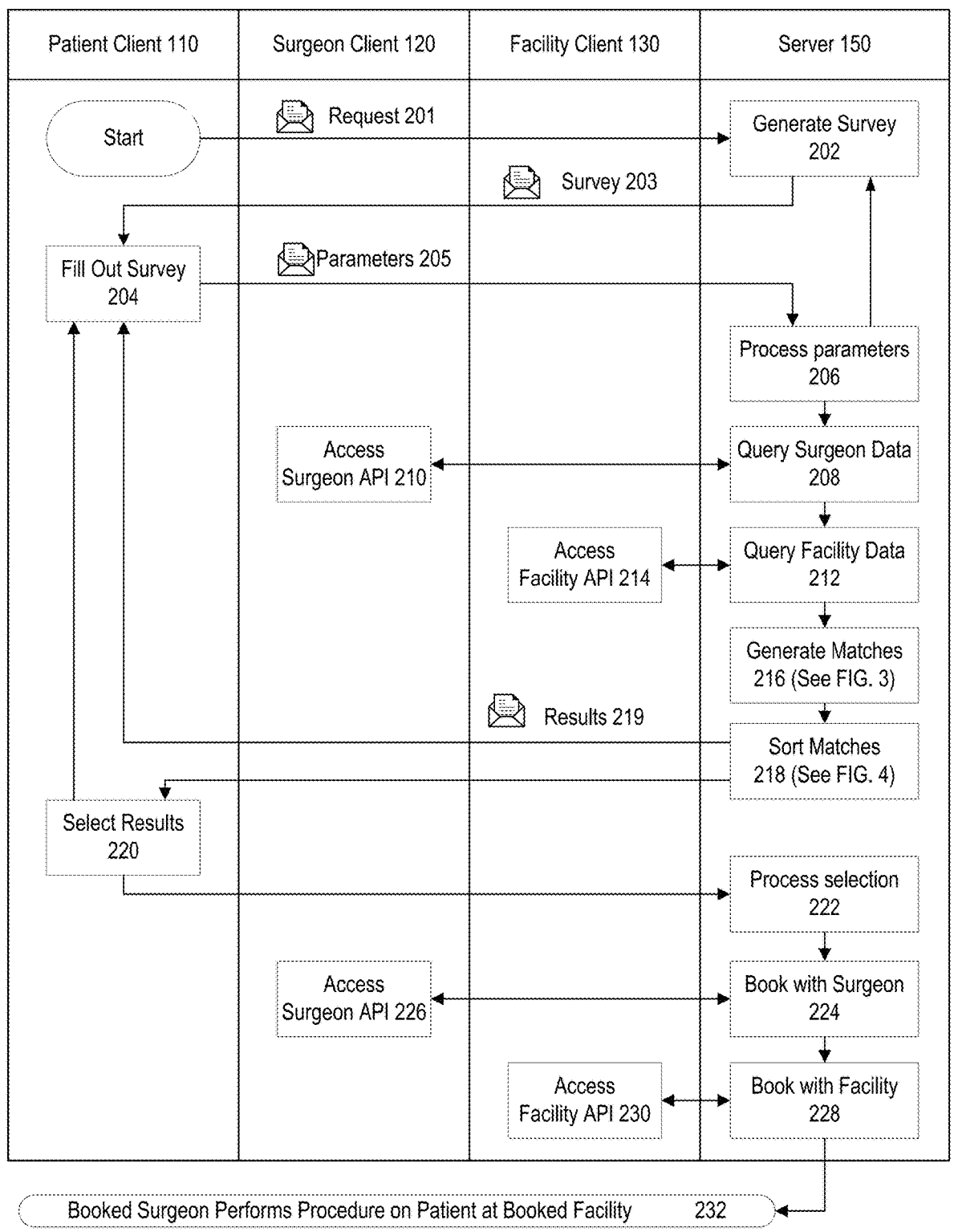
FIG. 2 illustrates an example surgical resource allocation process.

FIG. 2 illustrates an example process 200 for using the surgical resource allocation system 100. The process 200 is illustrated as a swim-lane flowchart showing operations performed by or at different components of the system 100, including the patient client 110, the surgeon client 120, the facility client 130, and the server 150. The illustrated process 200 also show various data objects flowing among the components of the system 100.

The process 200 can start with the flow moving to operation 202, which recites "generate survey." Following operation 202, the flow can move to operation 204, which recites "fill out survey." Following operation 204, the flow can move to operation 206, which recites "process parameters." Following operation 206, the flow can move to operation 202 or operation 208, which recites "query surgeon data." Operation 208 can include operation 210, which recites "access surgeon API." Following operation 208, the flow can move to operation 212, which recites "query facility data." Operation 212 can include operation 214, which recites "access facility API." Following operation 212, the flow can move to operation 216, which recites "generate matches." Following operation 216, the flow can move to operation 218, which recites "sort matches." Following operation 218, the flow can move to operation 204 or operation 220, which recites "select results." Following operation 220, the flow can move to operation 204 or operation 222, which recites "process selection." Following operation 222, the flow can move to operation 224, which recites "book with surgeon." Operation 224 can include operation 226, which recites "access surgeon API." Following operation 224, the flow can move to operation 228, which recites "book with facility." Operation 228 can include operation 230, which recites "access facility API." Following operation 228, the flow can move to operation 232, which recites "booked surgeon performs procedure on patient at booked facility."

A patient 10 can start the process 200 when he or she is seeking a surgeon 20, a facility 30, a procedure, or combinations thereof. The process 200 can begin with various preparatory steps, including but not limited to the patient 10 using the system interface 112 of the patient client 110 to access the server 150. For example, where the patient client 110 is a desktop computer, the patient 10 can launch a web browser and navigate to a website associated with the server 150 and configured as the system interface 112.

Accessing the server 150 can include, for example, the patient 10 registering with the server 150. The registration process can include the patient 10 providing information to the server 150, such as contact information, medical information, preferences, authentication information, or other data of the patient 10. If the patient 10 is already registered, accessing the server 150 can include the patient 10 authenticating with the server 150 by providing authentication information, such as a username and password.

After accessing the server 150, the patient 10 can prepare and submit a request 201. For example, the patient 10 can use the system interface 112 to prepare and submit the request 201 to the server 150 using an interface of the server 150. The request 201 can be a request for treatment associated with a particular condition, a request for a type of surgical procedure, a request for a specific surgical procedure, a request to book surgical services, a request for information regarding one or more surgeons 20, a request for information regarding one or more facilities 30, a request for one or more matches among the surgeons 20 and the facilities 30, or another request. The request 201 can include information regarding the patient 10, parameters of the request 201, or other information. For example, the request 201 can include information associated with a desired location for a procedure. The information can include, for example, a current location of the patient (e.g., as identified by a GPS receiver associated with the patient 10 or as specified by the patient via a current address, zip code, city, or state), a location where the patient 10 would like the procedure to be performed (e.g., as specified by an address, zip code, city or state), a distance from the location that the facility 30 can be, and other data. The information can also include financial information, such as a range of values that the patient 10 is willing to pay for the procedure. The information can also include scheduling information, such as a range of dates or times that the patient 10 is or is not available for the procedure or associated appointments.

After the process begins, the flow can move to operation 202, which recites "generate survey." At operation 202, the server 150 can receive the request 201 and, responsive to receiving the request 201, generate a survey 203. The survey 203 can include requests for information from the patient 10 regarding the request 201. The survey can include free-response questions, multiple-choice questions, or other questions.

For example, the survey 203 can include requests for information that was not provided as part of the request 201 or for follow up information related to information provided in the request 201.

In an example, in the request 201, the patient 10 may have requested to book a surgical procedure, and server 150 can generate a survey 203 that includes questions for obtaining information from the patient 10 regarding: a desired type of surgical procedure, when the patient 10 would like the surgical procedure to be performed, where the patient 10 would like the surgical procedure to be performed, preferences regarding a surgeon 20, preferences regarding a facility 30. In some examples, the survey 203 can also request patient 10 medical information directly or request authorization from the patient 10 for one or more components of the server 150 to access medical records associated with the patient 10.

Operation 202 can further include causing the survey 203 to be provided to the patient 10. This can include, for example, the server 150 sending the survey 203 to the patient client 110 for presenting to the patient 10 over the system interface 112.

Operation 204, which recites "fill out survey," can follow operation 204. At operation 204, the survey 203 can be received by the patient 10 and the patient 10 can prepare a response to the survey 203. For example, the patient 10 can access the survey using the system interface 112. The patient 10 can then use the system interface 112 prepare the response to the survey 203.

The at least partially filled-out survey 203 can be provided as parameters 205 to the server 150. In an example, the patient client 110 can send the parameters 205 to the server 150 using the system interface 112.

Operation 206, which recites "process parameters" can follow operation 204. At operation 206, the server 150 can receive the parameters 205. The server 150 can then process the parameters 205 to determine, for example, whether there are any incomplete, inconsistent, or missing information in the parameters 205. Responsive to determining that there is incomplete, inconsistent, or missing information in the parameters 205, the flow can move back to operation 202 to generate another survey 203 based on the received parameters 205.

At operation 206, the server 150 can further determine what additional data is needed for completing the request 201. For example, where the request 201 is for matches between surgeons 20 and facilities 30, the server 150 can further determine what data is needed from surgeons 20 and facilities 30. Such data can include, for example, schedules, capabilities, preferences, and metadata associated with the surgeons 20 and facilities 30.

Operation 208, which recites "query surgeon data" can follow operation 206. At operation 208, the server 150 can query or otherwise access data regarding the surgeons 20. This can include accessing the surgeon data 152 to acquire data. This can also include querying third-party data sources to acquire information. The third party data sources can include data sources associated with the Centers for Medicare and Medicaid Services (CMS), data sources associated with the CMS Physician Quality Reporting System (PQRS), data sources associated with the American College of Surgeons, data sources associated with the World Health Organization, data sources associated with the Royal College of Surgeons, data sources associated with the Healthcare Cost and Utilization Project, data sources associated with the National Institute of Health, or other data sources.

Operation 208 can further include performing operation 210, which recites "access surgeon API." At operation 210, the server 150 can access an application programming interface (API) associated with respective surgeons 20 to acquire data associated with the respective surgeon 20. For example, the server 150 can access an API associated with a data source associated with a respective surgeons 20. The API can be an API for a practice management application, a scheduling application, or other programs associated with the surgeon 20.

In an example, one or more surgeons 20 can be registered with the server 150, such that the surgeons 20 grant permission to the server 150 to access data or access the surgeon API. This can include permission for the server 150 to access data associated with surgeon 20 stored by one or more third parties, access data available through a surgeon API, or other data.

Although accessing the surgeon API (e.g., at operation 210) is shown as being within the "Surgeon client 120" swim lane, accessing the API need not be performed at the surgeon client 120. Accessing the API may occur at, for example, a computing environment associated with a respective surgeon 20 separate from the surgeon client 120.

Operation 212, which recites "query facility data" can follow operation 208. At operation 212, the server 150 can query or otherwise access data regarding the facilities 30. This can include accessing the facility data 154 to acquire data. This can also include querying third-party data sources to acquire information, including one or more of the third party data sources discussed regarding operation 208.

Operation 212 can further include performing operation 214, which recites "access facility API." At operation 212, the server 150 can access an API associated with the facilities 30 to acquire data regarding respective facilities 30. For example, the server 150 can establish a connection with or otherwise access an API associated with the scheduling system 134 of a respective facility 30. The server 150 can use the API to acquire at least some of the scheduling data 136 of the facility 30. In another example, the API can be an API associated with a practice management application.

Although accessing the facility API (e.g., at operation 226) is shown as being within the "Facility client 130" swim lane, accessing the API need not be performed at the facility client 130. Accessing the API may occur at, for example, a computing environment associated with a respective facility 30 separate from the facility client 130.

Operation 216, which recites "generate matches" can follow operation 212. At operation 216, the matching engine 162 can use the data gathered in operation 206, operation 208, and operation 212 to generate one or more matches for the patient 10 based on the received parameters 205, among other data. Matches can refer to matches between the parameters 205 and one or more surgeons 20; matches between the parameters 205 and one or more facilities 30; and matches between the parameters 205, the one or more surgeons 20, and the one or more facilities 30. For example, the patient 10 can choose to find surgeons 20 first and the server 150 can receive parameters 205 for that search. The server 150 can then determine surgeons 120 that match the parameters 205. These results can be presented for selection by the patient 10 (see, e.g., operation 220). The patient 10 can then choose to select facilities 30 next based on the selected surgeon 20 and other parameters. Similarly, the patient 10 can choose to identify one or more facilities 30 first and then identify a surgeon 20. In another example, the matches can be groups of one or more surgeons 20 and facilities 30 that match the parameters. Operation 216 is discussed in further detail in FIG. 3.

Operation 218, which recites "sort matches," can follow operation 216. At operation 218 the sorting engine 164 can sort the generated matches. The matches can be sorted based on a variety of attributes including but not limited to surgeon rankings, facility rankings, time, location, cost, and other attributes. Operation 218 is discussed in further detail in FIG. 4. At or following operation 218, the sorted matches can be provided to the patient 10 in the form of results 219.

Upon receiving the results 219, the patient 10 can view the results using the system interface 112. If the patient 10 finds a match that the patient 10 would like to select, the flow can move to operation 220, which recites "select results," and the selected result can be provided to the server 150. If the patient 10 would like to change one or more of the parameters 205 used to produce the results 219, the flow can return to operation 204, where the patient 204 provides updated parameters 204 to the server 150.

In an example, the patient 10 can select a match and, responsive to the selection, the server 150 can provide to the patient 10 more information about the match. For instance, the patient can see other available dates or other procedure parameters that would work for the matched surgeon 20 and facilities 30.

Operation 222, which recites "process selection," can follow operation 220. At operation 222, the server 150 can process the selection from the patient 10 to begin the booking process. This can include requesting additional information from the patient (e.g., confirmation, billing information, etc.). The server 150 can also determine one or more surgeons 20 or facilities 30 associated with the selection to contact.

In addition, operation 222 can further include determining whether booking requirements are met. For example, a surgeon 20 or facility 30 associated with the match may require a pre-operation consultation with the patient 10 before the requested procedure is performed. Responsive to determining that a requirement is not met, the flow can move to one of the previous operations to meet the requirement. For example, where the requirement is a pre-operative consultation, the server 150 may send a survey 203 to the patient requesting information regarding scheduling the pre-operation consultation (e.g., information regarding dates, times, locations, etc.).

Operation 224, which recites "book with surgeon," can follow operation 222. At operation 224, the server 150 can initiate a booking process with one or more surgeons 20 based on the selected results and operation 222. Operation 224 can further include operation 226, which recites "access surgeon API." At operation 226, the server can use an API associated with the surgeon to book the surgery with the surgeon 20.

Operation 228, which recites "book with facility," can follow operation 224. At operation 228, the server 150 can initiate a booking process with one or more facilities 30. Operation 228 can further include operation 230, which recites "access facility API." At operation 230, the server 150 can use an API associated with the one or more facilities 30 to book the surgery with the facility 30.

Operation 232, which recites "booked surgeon performs procedure on patient at booked facility," can follow operation 228. At operation 232, the one or more booked surgeons 20 may perform the procedure on the patient 10 at the booked facility 30.

Figure 3:
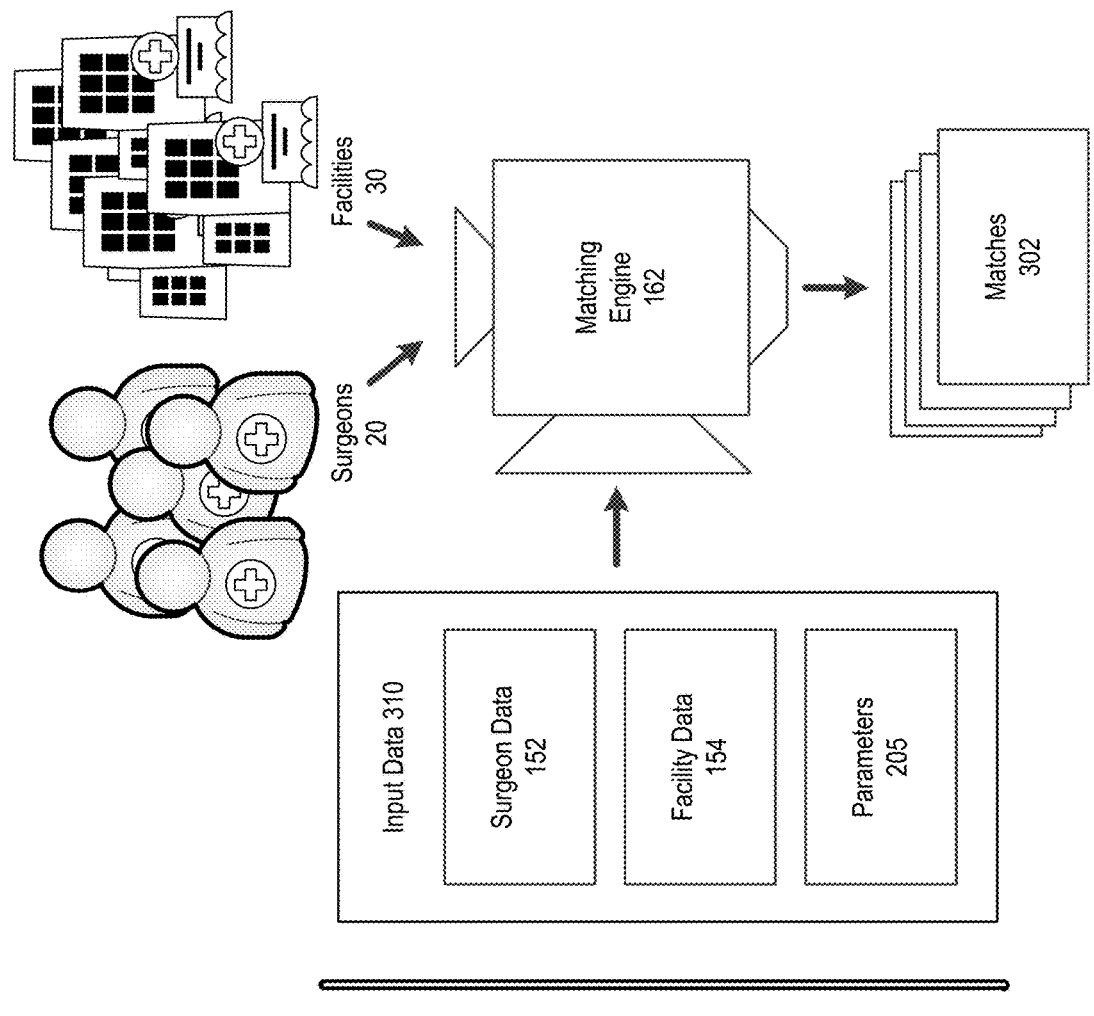
FIG. 3 illustrates an example method for matching surgeons and facilities.
Figure 3:
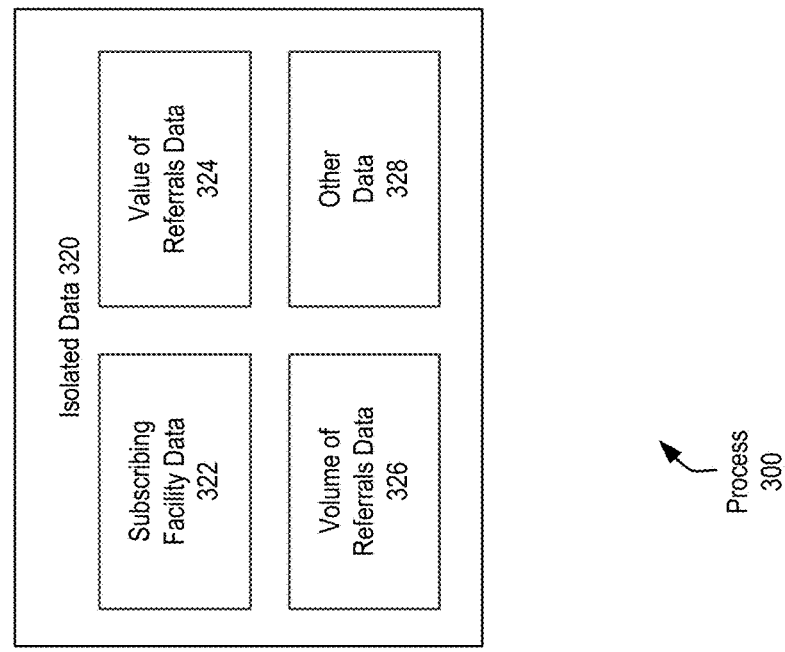

FIG. 3 illustrates an example process 300 for matching surgeons 20 and facilities 30 using the matching engine 162. The process 300 can produce one or more matches 302 as output. Each match of the matches 302 can be a compatible grouping of one or more surgeons 20 and one or more facilities 30. In a simple example, a match can be between one surgeon 20 and one facility 30. In another example, more complicated procedures may require multiple surgeons 20 and multiple facilities 30.

A match can be compatible if the members of the match would be able to cooperate as part of the requested procedure without violating their respective requirements or the requirements of the patient 10.

In another example, the matches 302 can be matches between the parameters 205 and one or more surgeons 20 or matches between the parameters 205 and one or more facilities 30. For example, where the patient 10 chooses to find a facility 30 first, the server 150 can generate a list of surgeons that match the parameters 205.

For example, a match can be compatible if the one or more surgeons 20 of the match could perform a requested procedure at the one or more facilities 30 of the match. Examples of causes of incompatibility can include a group where the members do not meet each other's requirements. For instance, a facility 30 can have certain requirements for surgeons 20 performing procedures (e.g., admitting privileges, qualifications, licensing requirements, etc.), and a compatible match would not include surgeons 20 failing to meet the requirements of the facilities 30. Similarly, a surgeon 20 can have certain requirements for facilities 30 at which the procedure can be performed. For example, the surgeon 20 can have travel requirements (e.g., the surgeon 20 may not want to travel more than a threshold distance to perform the procedure), the surgeon 20 can have certain equipment, staffing, or other resource requirements for prospective facilities 30. A compatible match would not include surgeons 20 that fail to meet the requirements of facilities 30.

A match can also be compatible with respect to the requirements of the patient 10. For example, the patient 10 can specify requirements (e.g., as part of parameters 205) relating to travel distance, procedure cost, insurance coverage, surgeon experience level, surgeon ranking, facility amenities, facility ranking, and other requirements.

A grouping can also be compatible with respect to the requirements of the procedure. For example, the grouped surgeons 20 and facilities 30 must be able to perform their respective aspect of the procedure.

The data regarding the requirements of the patient 10, surgeons 20, and facilities 30 can be provided as input data 310 to the matching engine 162. The input data 310 can include, for example, the surgeon data 152, the facility data 154, and the parameters 205.

In certain embodiments, some data can be isolated from the input data 310 such that isolated data 320 is not used by the matching engine 162 to generate matches. The isolated data 320 can include, but need not be limited to subscribing facility data 322, value of referrals data 324, volume of referrals data 326, and other data 328.

The subscribing facility data 342 can include data regarding whether particular facilities 30 are subscribing facilities 30. A subscribing facility 30 can be a facility 30 that is registered with the server 150 or a facility 30 that provides the server 150 with access to data (e.g., access to scheduling resources). The subscribing facility data 342 can also include data regarding an amount of money received from particular facilities 30 providing services associated with the server 150.

The value of referrals data 324 can include data related to a value associated with procedures referred to particular surgeons 20 or facilities 30. The volume of referrals data 326 can include data related to a number of referrals to or from particular surgeons 20 or facilities 30.

Separating isolated data 320 from input data 310 can provide technical advantages to the process 300. By reducing the amount of input data 310 entering the reward engine 166, fewer memory and processing resources are needed to generate the matches 302. This can, among other things, reduce the amount of computed resources needed to produce the matches 302. Separating the isolated data 320 from the input data 310 can also result in improvements to security, because the isolated data 320 can remain securely stored (e.g., encrypted) while the input data 310 is accessed and used in functions (e.g., in a decrypted form) to produce a result.

Separating isolated data 320 from input data 310 can also provide regulatory advantages to the process 300. For example, in some jurisdictions some or all of the isolated data 620 may be prohibited from being factored into matching surgeons 20 and facilities 30. By separating the isolated data 320 from input data 310, the resulting matches 302 can be in compliance with regulations.

In an example, the matching engine 162 can produce matches by identifying a set of requirements associated with the patient 10 (e.g., maximum cost). For each requirement in the set of requirements, the matching engine 162 can iterate through the surgeons 20 and facilities 30 and eliminate surgeons 20 or facilities 30 that do not meet the requirement. For example, the patient 10 may be willing to travel no more than fifteen miles for the procedure, so one of the requirements could be that the location of the facility 30 is less than fifteen miles from the patient's home. To ensure, that the matches 302 meet this requirement, the matching engine 162 can iterate through the list of possible facilities 30 and remove any facility 30 that is more than fifteen miles from the patient's home. In an example, the matching engine 162 can then iterate through the surgeons 20 and remove any surgeons that are unable to perform the procedure at the remaining facilities 30.

In another example, the matching engine 162 can treat the problem of generating matches 302 as a kind of constraint satisfaction problem and solve accordingly.

Figure 4:
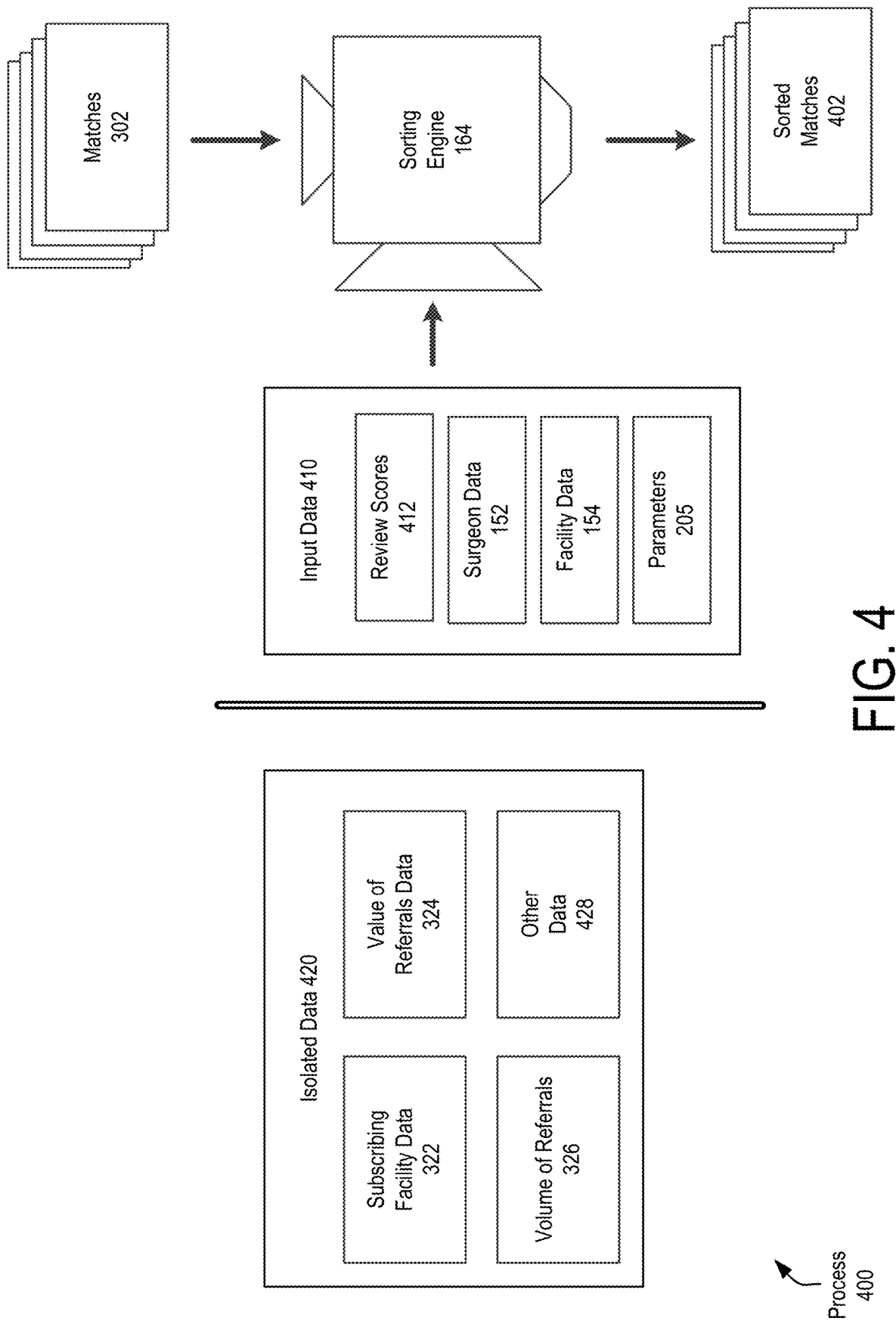
FIG. 4 illustrates an example method for sorting matches.

FIG. 4 illustrates an example process 400 for sorting the matches 302 using the sorting engine 164. The process 400 can produce sorted matches 402 as output. The sorting engine 164 can take input data 410 and the matches 302 as input to produce the resulting sorted matches.

The input data 410 can include review scores 412, surgeon data 152, facility data 154, parameters 205. The review scores 412 can include scores based on reviews or other evaluations performed on surgeons or facilities. The input data 410 can also include other data, such as surgeon attributes or facility attributes.

In certain embodiments, some data can be isolated from the input data 410, such that isolated data 420 is not used by the sorting engine 164 to generate the sorted matches 402. The isolated data 420 can include the subscribing facility data 322, the value of referrals data 324, the volume of referrals data 326, and other data 428.

Separating isolated data 420 from input data 410 provides technical advantages to the process 400. By reducing the amount of input data 410 entering the sorting engine 164, fewer memory and processing resources are needed to generate the sorted matches 402. This can, among other things, reduce the amount of computed resources needed to produce the sorted matches 402. Separating the isolated data 420 from the input data 410 can also result in improvements to security, because the isolated data 420 can remain securely stored while the input data 410 is accessed and used in functions to produce a result.

Separating isolated data 420 from input data 410 can also provide regulatory advantages to the process 400. For example, in some jurisdictions some or all of the isolated data 420 may be prohibited from being factored into sorting matches. By separating the isolated data 420 from input data 410, the resulting sorted matches 402 can be in compliance with regulations.

In an example, the sorting engine 164 can sort matches based on attributes of the matches 302. For instance, the patient 10 may want to view the matches 302 sorted by ranking, distance, cost, or another attribute of the matches 302. In those instances, the sorting engine 164 can simply order the matches 302 using a sorting algorithm according to the attribute to generate the sorted matches 402.

In another example, the sorting engine 164 can score the matches 302 and then sort the matches 302 according to the score. For example, the sorting engine 164 can generate a score that takes into account the respective rankings of the surgeon 20 and facilities 30 in a respective match. This score could be for example an average of the respective rankings. In another example, the score can take into account other attributes, such as amenities of the facility 30, years of experience of the surgeon, or other attributes.

Figure 5:
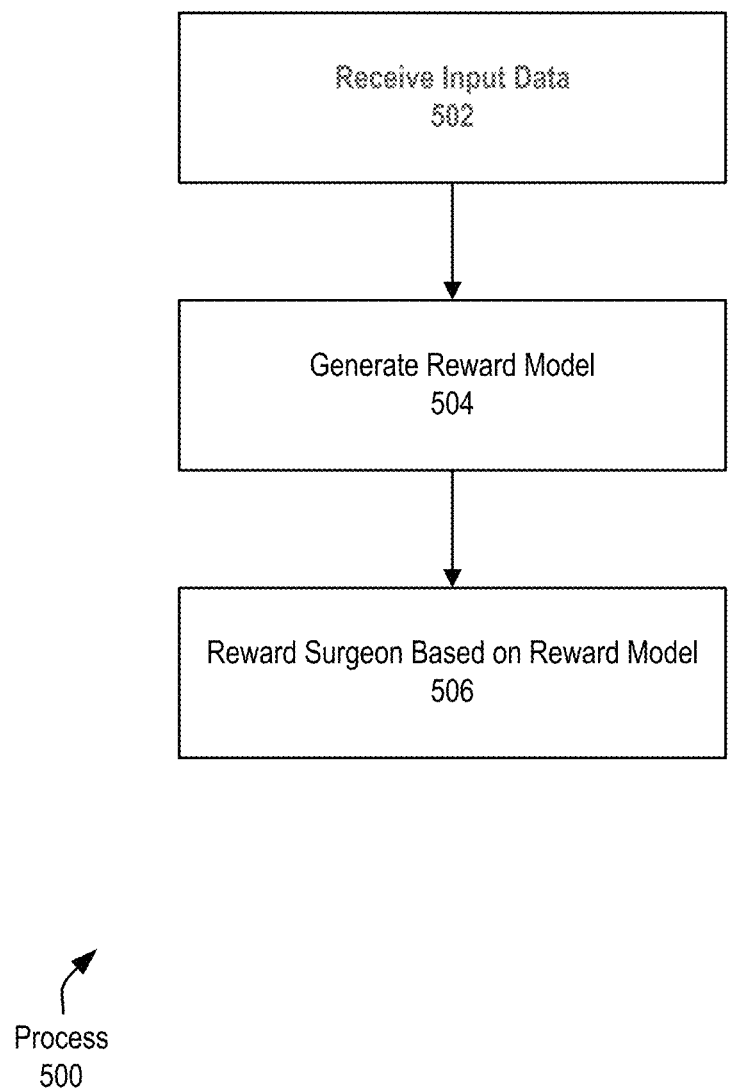
FIG. 5 illustrates an example method for rewarding surgeons based on a reward model.

FIG. 5 illustrates an example process 500 for rewarding a surgeon 20 based on a reward model. For example, the process 500 can be performed for each surgeon 20 of a plurality of surgeons 20. The process 500 can begin with operation 502, which recites "receive input data." After operation 502, the flow can move to operation 504, which recites "generate reward model." After operation 506, the flow can move to operation 506, which recites "reward surgeon based on reward model."

The process can begin with operation 502, which recites, "receive input data." At operation 502, the server 150 can receive or retrieve (e.g., from the surgeon data 152) input data for use in generating the reward model. The input data can include a variety of data, including surgeon attribute data and reviews for surgeons.

For example, the surgeon attribute data describing attributes of one or more surgeons. The surgeon attribute data can include, for example, data collected from or generated based on passive data collection methods. This can include biometric data gathered from devices with biometric sensors, such as wearable devices. The biometric data can be used to infer patient anxiety or other patient health information. The inferred patient anxiety or other patient health information can be used to score surgeon attributes, such as bedside manner, effectiveness, efficiency, and others.

The input data can include one or more reviews for the surgeon 20. In an example, the server 150 can send a request for a review of a surgeon 20 to a patient 10 that received services from the surgeon 20. For example, the server 150 can cause a paper questionnaire to be provided to the patient 10 at home or while the patient 10 is at the facility 30. In another example, the server 150 can cause a person to interview the patient 10 regarding the services performed, such as via telephone or in-person. In another example, the server 150 can send an electronic message containing the questionnaire to the patient 10 using patient-provided contact information.

The questionnaire can ask the patient 10 to provide information regarding the surgeon 20 that performed the procedure. This information can include, for example, bedside manner, timeliness, professionalism, and other information. Information can also include information regarding a quality of the procedure performed, such as a recovery time, a discomfort level, a satisfaction with the results, and other information. The questionnaires can also ask the patient 10 about the facility 30 at which the procedure was performed.

In another example, questionnaires can also be provided to people who worked with the surgeon 20 on the particular procedure. For example, questionnaires can be provided to staff of the facility 30 with which the surgeon 20 interacted for the procedure.

The server 150 can then receive the results of these questionnaires. For example, the patient 10 can provide the results of the completed questionnaire via electronic message, via phone call, via return mail. In another example, where a third-party asked the patient 10 questions regarding the surgeon 20, the third party can provide the results to the server 150. The server 150 can store the received questionnaires, for example, as part of the surgeon data 152, the facility data 154, and/or the patient data 156.

The completed questionnaires can be received at the server 150 as completed reviews of the surgeon 20.

In some examples, the patient 10 can be asked to explicitly rate aspects of the surgeon 20 or facility 30. In some examples, the server 150 can perform operations on the reviews to, for instance, standardize the reviews or generate new reviews based on the received reviews. In an example, the server 150 can average different aspects of a patient's rating of the surgeon 20. For instance, the questionnaire may ask the patient 10 to rank the surgeon 20 with regard to timeliness, professionalism, and satisfaction with the results. The server 150 can generate an overall review of the surgeon 20 based on the individual scores for the timeliness, professionalism, and satisfaction ratings. In another example, the server 150 can generate a new review for the surgeon 20 based on patient population health metrics that are inferred or determined based on the received reviews. In yet another example, the server 150 can analyze comments or qualitative descriptors in the received questionnaire results and used machine learning (e.g., sentiment analysis) to generate a ranking based on the analyze comments or descriptors.

In some examples, the reviews need not be from the patient 10. Instead reviews can be received from people who worked with the surgeon 20. For example, support staff at the facility 30 at which the surgeon 20 performed the procedure on the patient 10.

In an example, the server 150 can sanitize the received review data. For instance, the server 150 can remove data that should not be factored into the reward process, such as the isolated data 320 or the isolated data 420 (see also isolated data 620).

Operation 504, which recites "generate reward model," can follow operation 502. A reward model can specify an amount or manner in which a surgeon 20 is to be rewarded. For example, a reward model may indicate that a particular surgeon 20 should receive a reward of $1,000.

In an example, the reward model can be generated based, in part, on the input data. For example, surgeons 20 that receive high ratings from the received reviews can receive higher rewards than surgeons 20 that receive lower reviews. In another example, surgeons 20 that cause their patients to have biometric readings that are comparatively better can receive higher rewards. For instance, a surgeon whose patients have better biometric readings (e.g., lower anxiety levels before, during, or after an interaction with the surgeon) than similarly situated patients with other surgeons can receive a higher reward. In another example, the server 150 may require that the a minimum number of reviews be received regarding a respective surgeon 20 for the surgeon 20 to receive a reward. For instance, the server 150 may have to have received ten reviews for a particular surgeon 20 in order for the surgeon 20 to be eligible for a reward. In another example, the server 150 may require that the surgeon have received an average score that exceeds a threshold. For instance, if the surgeon 20 is graded on a five-point scale, a threshold of a 3.0 average score can be required for the surgeon 20 receive a reward. An example process for generating a reward model using the reward engine 166 is discussed with regard to FIG. 6.

Operation 506, which recites "reward surgeon based on reward model," can follow operation 504. At operation 506, the surgeon 20 can be provided with a reward based on the reward model. The reward can include monetary and/or non-monetary components. An example process for rewarding a surgeon 20 based on the reward model is discussed with regard to FIG. 7.

Figure 6:
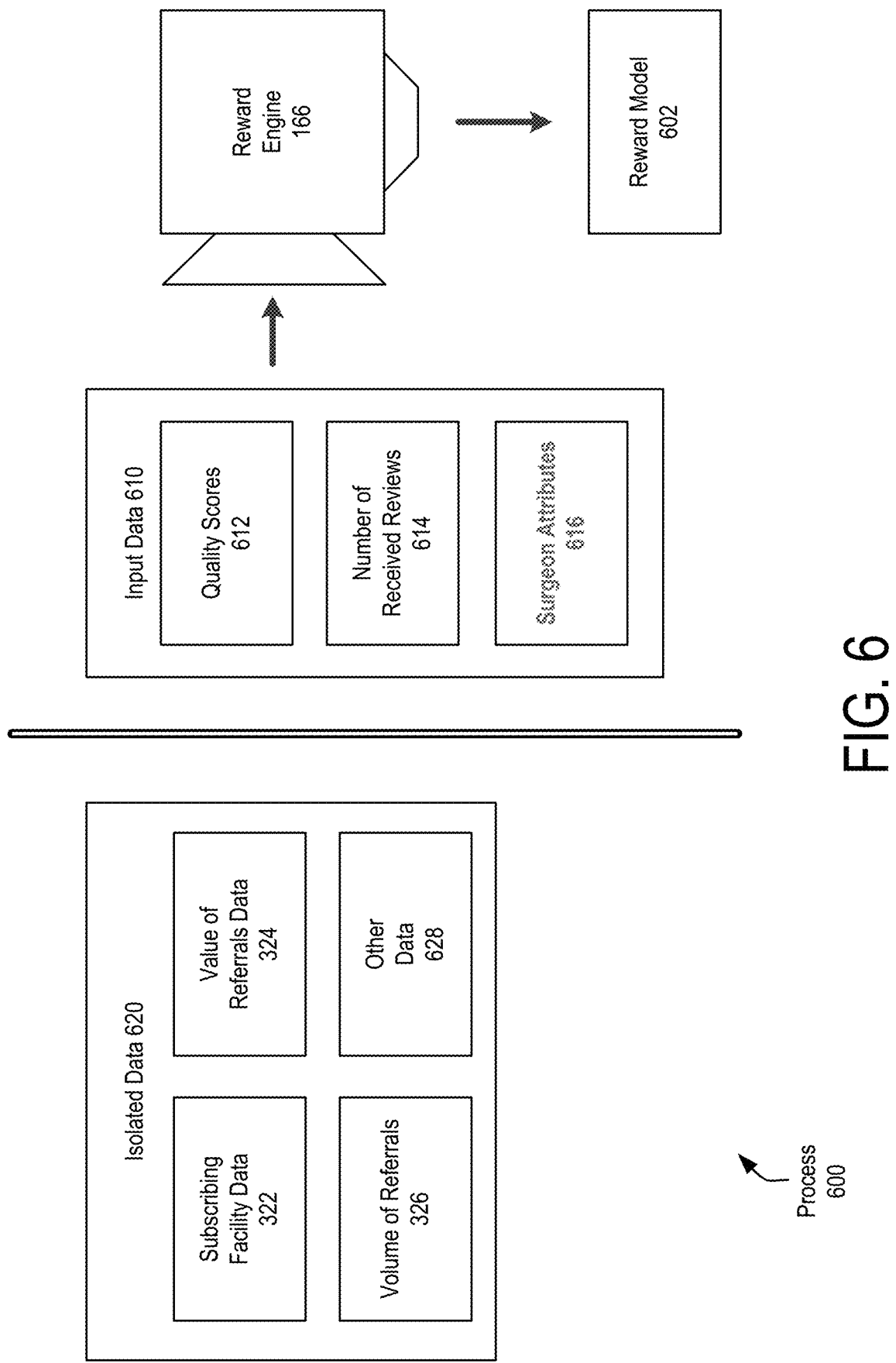
FIG. 6 illustrates an example method for generating a reward model.

FIG. 6 illustrates an example process 600 for generating a reward model 602 using the reward engine 166 based on the input data 610. The input data 610 can include, for example, data based on the received reviews, such as quality scores 612, a number of reviews received 614, and other data. The input data 610 can also include surgeon attributes 616. In some embodiments, data can be isolated from the input data 610 such that the reward model does not use isolated data 620 to produce the reward model 602. The isolated data 620 can include subscribing facility data 342, value of referrals data 324, volume of referrals data 326, and other data 628.

Separating isolated data 620 from input data 610 provides technical advantages to the process 600. By reducing the amount of input data 610 entering the reward engine 166, fewer memory and processing resources are needed to generate the reward model 602. This can, among other things, reduce the amount of computed resources needed to produce the reward model 602. Separating the isolated data 620 from the input data 610 can also result in improvements to security, because the isolated data 620 can remain securely stored while the input data 610 is accessed and used in functions to produce a result.

Separating isolated data 620 from input data 610 can also provide regulatory advantages to the process 600. For example, in some jurisdictions some or all of the isolated data 620 may be prohibited from being factored into rewarding surgeons 20. By separating the isolated data 620 from input data 610, the resulting reward model 602 can be in compliance with required regulations.

Figure 7:
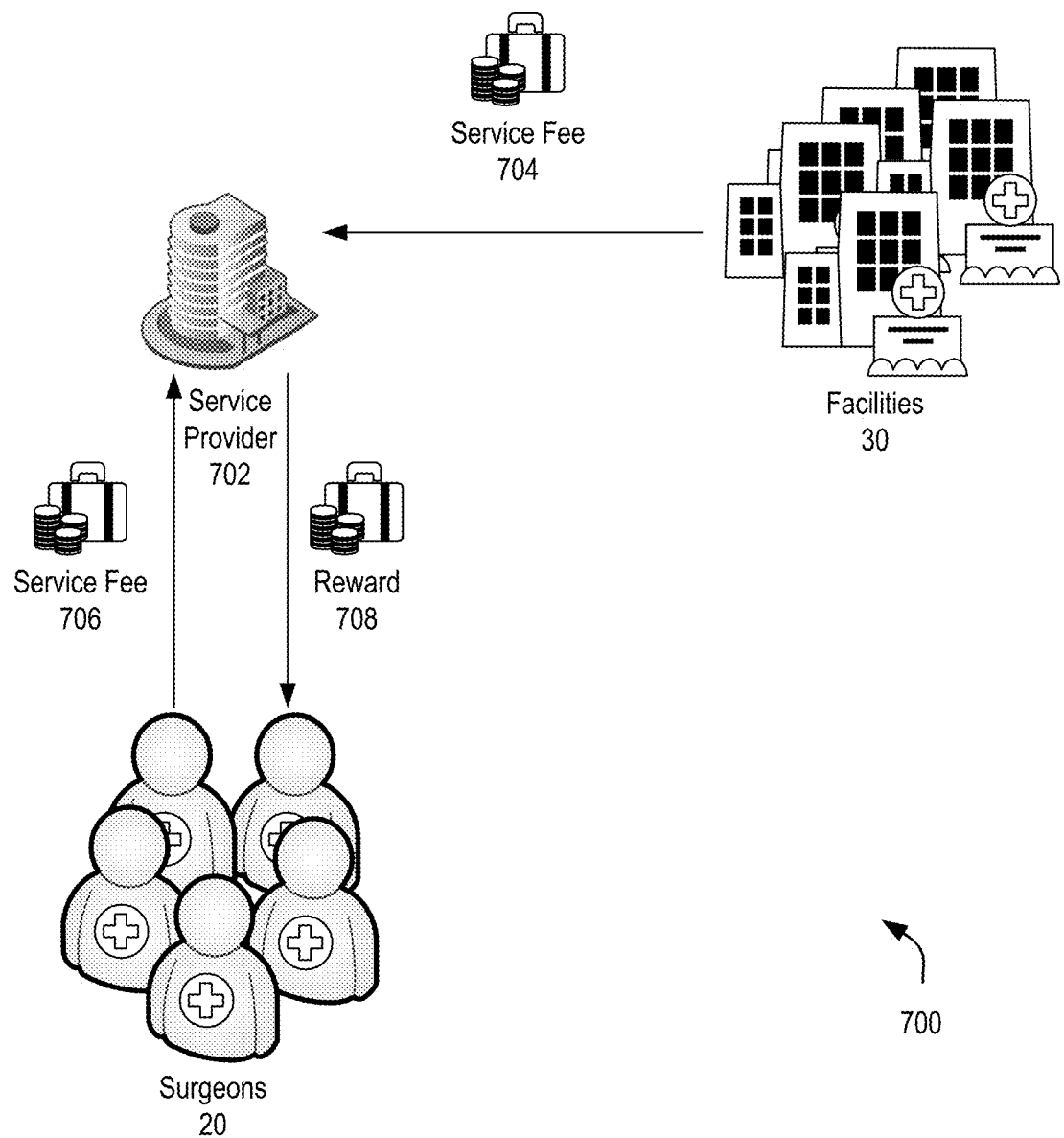
FIG. 7 illustrates an example fee and reward flow.

FIG. 7 illustrates an example fee and reward flow 700. A matching service provider 702 (e.g., a provider that facilitates the service shown and describe with regard to FIG. 1 and FIG. 2) can receive a service fee 704 from subscribing facilities 30. The provider 702 can also receive a service fee from the surgeons 20. The service provider 702 can provide a reward 708 to the surgeon 20 based on a reward model (e.g., reward model 602).

In an example, the service provider 702 may have a policy to not exclude as a participant, any individual (e.g., a surgeon 20) or entity (e.g., a facility 30) that would otherwise meet qualifications for participation.

In another example, the service provider 702 may assess the service fee 704 equally across the surgeons 20. The service fee 706 may be assessed equally across the facilities 30. In an example, the service fee 704 and the service fee 706 are based on the cost of operating the matching service. In an example, the service fee 704 and the service fee 706 are not based on a volume or value of any referrals to or business otherwise generated by the surgeons 20 and the facilities 30. In an example, the service fee 704 and the service fee 706 are not based on a volume or value of any referrals to or business otherwise generated by the surgeons 20 and the facilities 30 for which payment may be made in whole or in part under Medicare, Medicaid, or other federal health care programs.

In an example, the service provider 702 imposes no requirements on the manner in which the participants (e.g., surgeons 20 or facilities 30) provide services to patients 10, other than requiring that the participants charge the patient 10 at the same rate as it charges other persons not referred by the service provider 702, or that these services be furnished free of charge or at reduced charge.

In an example, the service provider 702 may make a series of disclosures to patients seeking a match using the service provider 702. The service provider 702 may maintain a record of the disclosures (e.g., certifying such a disclosure was made and/or signed by either such person seeking a referral or by the individual making the disclosure on behalf of the referral service). The record may be, for example, stored using the server 150.

The disclosures may include one or more disclosures described by 42 CFR § 1001.952 (f), incorporated herein by reference for any and all purposes.

The disclosures may include the manner in which fit the service provider 702 selects the group of participants in the referral service to which it could make a referral. The disclosures may further include whether the participant has paid a fee to the referral service. The disclosures may further include the manner in which the service provider 702 selects a particular participant from the group for the patient 10. The disclosures may further include the nature of the relationship between the referral service and the group of participants to whom it could make the referral. The disclosures may further include the nature of any restrictions that would exclude such an individual or entity from continuing as a participant.

In some examples, the service provider 702 is not a health care provider or a health care supplier. In an example, the service provider 702 is not affiliated with the health care industry other than through establishing matches and booking the procedures. In an example, the service provider 702 does not target patients 10 with a particular healthcare payor program. In an example, service fee 704 and the service fee 706 are not based on whether the patient 10 becomes a patient of a particular surgeon 20 or facility 30. In an example, the service provider 702 does not steer patients to particular surgeons 20 or facilities 30. In an example, the service provider 702 does not steer patients to particular surgeons 20 or facilities 30 based on fees paid by the surgeons 20 or facilities 30.

Figure 8:
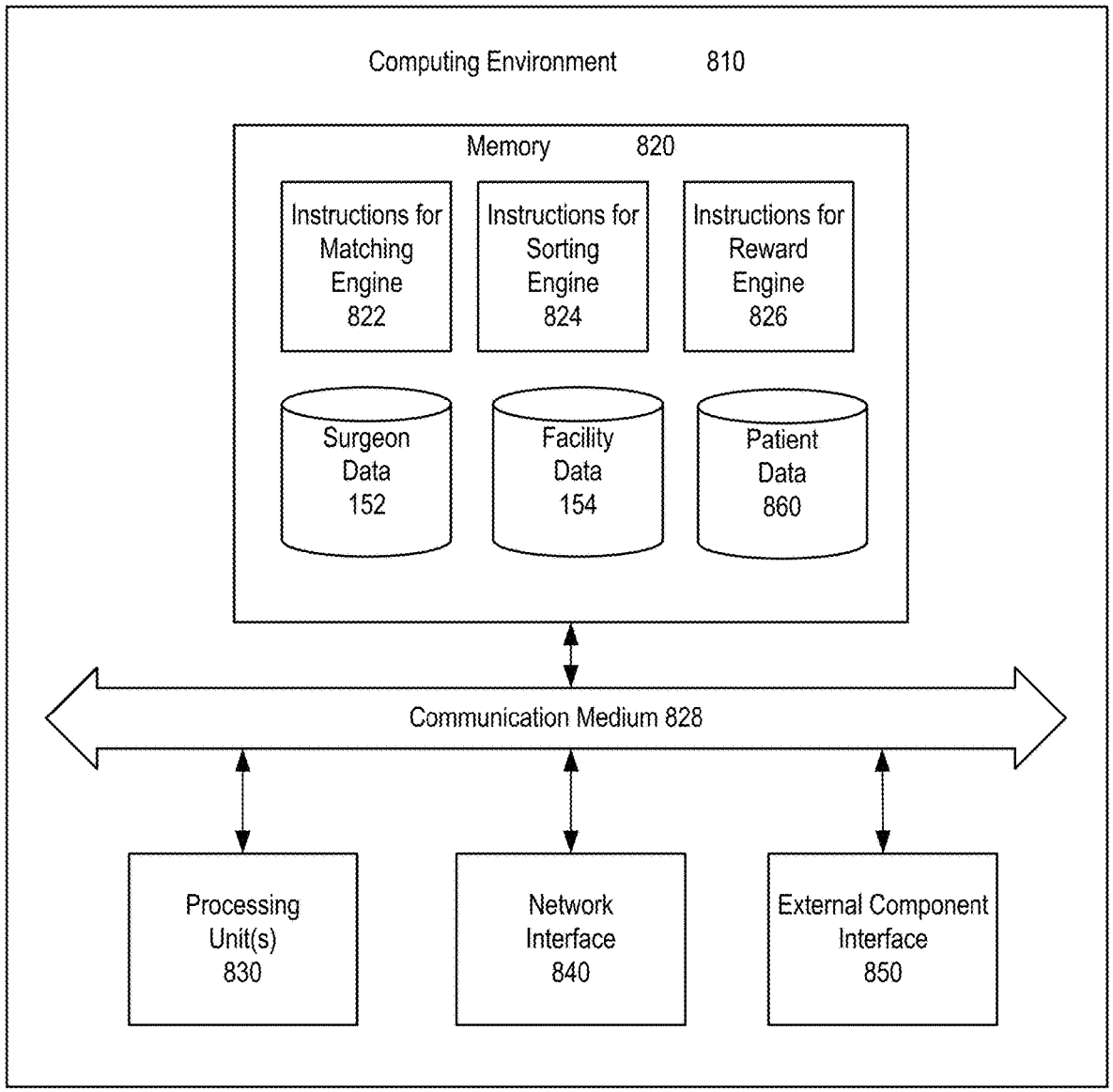
FIG. 8 illustrates an example computing system with which disclosed systems and methods can be used.

FIG. 8 illustrates an example system 800 with which disclosed systems and methods can be used. In an example, the patient client 110, the surgeon client 120, the facility client 130, and the server 150 can be implemented as one or more systems 800. In an example, the system 800 can include a computing environment 810, surgeon data 152, facility data 154, and patient data 860. The computing environment 810 can be a physical computing environment, a virtualized computing environment, or a combination thereof. The computing environment 810 can include memory 820, a communication medium 828, one or more processing units 830, a network interface 840, and an external component interface 850.

The memory 820 can include a computer readable storage medium. The computer storage medium can be a device or article of manufacture that stores data and/or computer-executable instructions. The memory 820 can include volatile and nonvolatile, transitory and non-transitory, removable and non-removable devices or articles of manufacture implemented in any method or technology for storage of information, such as computer readable instructions, data structures, program modules, or other data. By way of example, and not limitation, computer storage media may include dynamic random access memory (DRAM), double data rate synchronous dynamic random access memory (DDR SDRAM), reduced latency DRAM, DDR2 SDRAM, DDR3 SDRAM, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data.

The memory 820 can store various types of data and software. For example, as illustrated, the memory 820 includes instructions 822 for implementing the matching engine 162, instructions 824 for implementing the sorting engine 164, and instructions 826 for implementing the reward engine 166. The memory 820 can also include the surgeon data 152, the facility data 154, and the patient data 860.

The communication medium 828 can facilitate communication among the components of the computing environment 810. In an example, the communication medium 828 can facilitate communication among the memory 820, the one or more processing units 830, the network interface 840, and the external component interface 850. The communications medium 828 can be implemented in a variety of ways, including but not limited to a PCI bus, a PCI express bus accelerated graphics port (AGP) bus, a serial Advanced Technology Attachment (ATA) interconnect, a parallel ATA interconnect, a Fiber Channel interconnect, a USB bus, a Small Computing system interface (SCSI) interface, or another type of communications medium.

The one or more processing units 830 can include physical or virtual units that selectively execute software instructions. In an example, the one or more processing units 830 can be physical products comprising one or more integrated circuits. The one or more processing units 830 can be implemented as one or more processing cores. In another example, one or more processing units 830 one or more separate microprocessors. In yet another example embodiment, the one or more processing units 830 can include an application-specific integrated circuit (ASIC) that provides specific functionality. In yet another example, the one or more processing units 830 provide specific functionality by using an ASIC and by executing computer-executable instructions.

The network interface 840 enables the computing environment 810 to send and receive data from a communication network (e.g., network 140). The network interface 840 can be implemented as an Ethernet interface, a token-ring network interface, a fiber optic network interface, a wireless network interface (e.g., WI-FI), or another type of network interface.

The external component interface 850 enables the computing environment 810 to communicate with external devices. For example, the external component interface 850 can be a USB interface, Thunderbolt interface, a Lightning interface, a serial port interface, a parallel port interface, a PS/2 interface, and/or another type of interface that enables the computing environment 810 to communicate with external devices. In various embodiments, the external component interface 850 enables the computing environment 810 to communicate with various external components, such as external storage devices, input devices, speakers, modems, media player docks, other computing devices, scanners, digital cameras, and fingerprint readers.

Although illustrated as being components of a single computing environment 810, the components of the computing environment 810 can be spread across multiple computing environments 810. For example, one or more of instructions or data stored on the memory 820 maybe stored partially or entirely in a separate computing environment 810 that is accessed over a network While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the technology. Accordingly, what is desired to be secured by Letters Patent is the technology as defined and differentiated in the following claims, and all equivalents.

I claim:

1. A method for generating matches between surgeons and surgical facilities, the method comprising:
   acquiring surgical facility data regarding two or more surgical facilities;
   obtaining surgeon data;
   receiving a request for surgical services for a patient from a client device, the request including patient parameters;
   isolating, from the obtained surgeon data, volume of referrals data for respective surgeons and value of referrals data for respective surgeons,
   generating one or more matches between surgeons and surgical facilities based in part on the surgical facility data and the patient parameters, and
   booking with a matching surgeon,
   wherein generating the one or more matches is further based in part on the obtained surgeon data remaining after the isolating.

2. The method of claim 1, further comprising:
   sorting the one or more matches using the surgical facility data, the patient parameters, scores associated with the surgeons, or scores associated with the surgical facilities;
   providing the one or more matches to the client device;
   receiving a selection of a match from the client device; and
   transmitting surgical services confirmation data to the client device, a surgeon device associated with the selection, and a surgical facility device associated with the selection.

3. The method of claim 1, further comprising:
   generating a reward model for one or more of the surgeons based in part on population health scores associated with the one or more surgeons.

4. The method of claim 1, further comprising:
   providing a set of surgeons to the client device, the set of surgeons selected based on the patient parameters; and
   receiving a selection of one or more surgeons from the provided set of surgeons,
   wherein the generated one or more matches is further based in part on data regarding the selected one or more surgeons.

5. The method of claim 1, wherein acquiring the surgical facility data comprises acquiring data regarding a plurality of subscribing surgical facilities and a plurality of non-subscribing surgical facilities,
   wherein the method further comprises anonymizing the surgical facility data with respect to whether a respective surgical facility is a subscribing surgical facility or a non-subscribing surgical facility; and
   wherein generating the one or more matches is based in part on the anonymized_surgical facility data.

6. A method for generating matches between surgeons and surgical facilities, the method comprising:
   acquiring surgical facility data for two or more surgical facilities, wherein acquiring the surgical facility data comprises establishing a connection with an application programming interface of a medical scheduling service associated with at least one of the surgical facilities;
   acquiring surgeon data for two or more surgeons;
   isolating, from the obtained surgeon data, volume of referrals data for respective surgeons and value of referrals data for respective surgeons,
   receiving, from a client device, a request for surgical services for a patient, the request comprising patient parameters;
   generating one or more matches between a surgeon and a surgical facility based in part on the surgical facility data, the surgeon data, and the patient parameters, and
   booking with a matching surgeon,
   wherein generating the one or more matches is further based in part on the obtained surgeon data remaining after the isolating.

7. The method of claim 6, wherein the surgeon data comprises data regarding admitting privileges for each of the surgeons, a number of times each of the surgeons has performed particular procedures, or a bedside manner rating of each of the surgeons.

8. The method of claim 7, further comprising:
   sorting the one or more matches using the surgeon data, the surgical facility data, the patient parameters, scores associated with respective surgeons, and scores associated with the surgical facilities.

9. The method of claim 6, wherein acquiring the surgical facility data for the two or more surgical facilities further comprises:
   for each respective surgical facility of a first set of one or more surgical facilities, establishing a connection with an application programming interface of a medical scheduling service associated with the respective surgical facility;
   acquiring first surgical facility data regarding the first set of surgical facilities, the first scheduling facility data comprising data acquired over the established connection;
   acquiring second surgical facility data regarding a second set of one or more surgical facilities, wherein a connection to a medical scheduling service has not been established with the surgical facilities of the second set of surgical facilities.

10. The method of claim 6, wherein the patient parameters comprises patient location data, a procedure type, a patient schedule, or patient insurance provider data.

11. The method of claim 6, further comprising:
   providing the one or more matches to the client device;
   receiving a selection of a match from the client device; and transmitting surgical services confirmation data to the client device, a surgeon associated with the selection, and a surgical facility associated with the selection.

* * * * *